United States Patent
Ptitsyn et al.

(10) Patent No.: US 6,991,924 B2
(45) Date of Patent: Jan. 31, 2006

(54) MUTANT CARBAMOYLPHOSPHATE SYNTHETASE AND METHOD FOR PRODUCING COMPOUNDS DERIVED FROM CARBAMOYLPHOSPHATE

(75) Inventors: Leonid Romanovich Ptitsyn, Moscow (RU); Sergey Vasil'evich Smirnov, Moscow (RU); Irina Borisovna Altman, Moscow (RU); Anna Eugenievna Novikova, Moscow (RU); Veronika Aleksandrovna Kotliarova, Moscow (RU); Mikhail Markovich Gusyatiner, Moscow (RU); Yulia Georgievna Rostova, Moscow (RU); Tatyana Abramovna Yampolskaya, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 545 days.

(21) Appl. No.: 10/210,115

(22) Filed: Aug. 2, 2002

(65) Prior Publication Data
US 2003/0129708 A1 Jul. 10, 2003

(30) Foreign Application Priority Data
Aug. 3, 2001 (RU) .............................. 2001121697

(51) Int. Cl.
*C12P 19/38* (2006.01)
*C12P 19/30* (2006.01)
*C12P 13/10* (2006.01)
*C12N 1/21* (2006.01)
*C12N 9/00* (2006.01)
*C07H 21/04* (2006.01)

(52) U.S. Cl. .................... 435/114; 435/87; 435/89; 435/183; 435/252.3; 435/252.33; 536/23.2

(58) Field of Classification Search ............... 536/23.2; 435/183, 252.3, 252.33, 114, 87, 89
See application file for complete search history.

(56) References Cited

OTHER PUBLICATIONS

Nyunoya et al. (1983) PNAS, vol. 80, pp. 4629-4633.*
J. B. Thoden, et al.,Biochemistry, vol. 36, No. 21, pp. 6305-6316, "Structure of Carbamoyl Phosphate Synthetase: a Journey of 96 a from Substrate to Product", 1997.
J. B. Thoden, et al., Acta Crystallographica, Section D, vol. 55, pp. 8-24, "The Structure of Carbamoyl Phospahate Synthetase Determined to 2.1 Åresolution", 1999.
S. Delannay, et al., J. Mol. Biol., vol. 286, pp. 1217-1228, "Serine 948 and Threonine 1042 are Crucial Residues for Allosteric Regulation of *Escherichia coli* Carbamoylphosphate Systhetase and Illustrate Coupling Effects of Activation and Inhibition Pathways", 1999.
F. R. Blattner, et al., Science, Accession No. AE000113 U00096, pp. 1-8, "the Complete Genome Sequence of *Escherichia coli* K-12", 1997 (Abstract only of vol. 277, No. 5331, pp. 1453-1474).

* cited by examiner

Primary Examiner—Elizabeth Slobodyansky
(74) Attorney, Agent, or Firm—Oblon, Spivak, McClelland, Maier & Neustadt, P.C.

(57) ABSTRACT

L-arginine, citrulline and pyrimidine derivatives including orotic acid, uridine, uridine 5'-monophosphate (UMP), cytidine and cytidine 5'-monophosphate (CMP) are produced using a bacterium belonging to the genus *Escherichia* harboring a mutant carbamoylphosphate synthetase in which the amino acid sequence corresponding to positions from 947 to 951 in a wild type carbamoylphosphate synthetase is replaced with any one of amino acid sequences of SEQ ID NOS: 1 to 9, and feedback inhibition by uridine 5'-monophosphate in the bacterium is desensitized.

12 Claims, 2 Drawing Sheets

Pool of mutant *AflII-SacI* fragments of *carB* gene

MUTANT CARBAMOYLPHOSPHATE SYNTHETASE AND METHOD FOR PRODUCING COMPOUNDS DERIVED FROM CARBAMOYLPHOSPHATE

BACKGROUND OF THE INVENTION

1. Field of the Invention

The present invention relates to microbiological industry, specifically to a method for producing compounds derived from carbamoylphosphate. More specifically, the present invention concerns the using of new feedback-resistant enzymes involved in arginine and pyrimidine biosynthesis pathways of *E.coli* strains producing compounds derived from carbamoylphosphate, such as arginine, citrulline and pyrimidine derivatives including orotic acid, uridine, uridine 5'-monophosphate (UMP), cytidine and cytidine 5'-monophosphate (CMP).

2. Description of the Related Art

The carbamoylphosphate synthetase (CPSase) of *E.coli* catalyzes the complex synthesis of carbamoylphosphate (CP) from bicarbonate, glutamine and two molecules of Mg-ATP, with the release of glutamate, phosphate, and two Mg-ADP [Meister A., *Advan. Enzymol. Mol. Biol.*, vol. 62, p. 315–374, 1989]. The synthesis of CP is intermediate for two biosynthetic pathways, namely those of pyrimidine nucleotides and arginine. In the first pathway, CP is coupled to aspartate carbamoyltransferase (ATCase), resulting in formation of orotate in two steps. Orotate is an important metabolic intermediate for the biosynthesis of pyrimidine derivatives, including pyrimidines, such as uracil; pyrimidine nucleosides, such as orotidine, uridine, and cytidine; and pyrimidine nucleotides, such as orotidine 5'-monophosphate (OMP), UMP, and CMP. It was shown that the presence of orotate in a culturing medium during fermentation of the wide scope of bacteria assists measurably in the production and accumulation of pyrimidine derivative, namely, uracil (U.S. Pat. No. 3,214,344). In the second pathway, CP is coupled to ornitine via ornitine carbamoyltransferase (OTCase), constituting the sixth step (starting from glutamate) in the arginine biosynthetic pathway. CPSase is activated by ornitine and IMP (a precursor of purine nucleotides) and inhibited by UMP. Carbamoylphosphate synthetase consists of two subunits. It has been known for coryneform bacteria (EP1026247A1) and for bacteria belonging to the genera *Escherichia* and *Bacillus* that those subunits are encoded by carA and carB genes. Transcription of the carAB operon is cumulatively repressed by the end-products of both pathways [Charlier D., et al., *J. Mol. Biol.*, vol. 226, p. 367–386, 1992; Wang H., et al., *J. Mol. Biol.*, vol. 277, p. 805–824, 1998; Glansdorff N., et al., *Paths to Pyrimidines*, vol. 6, p. 53–62, 1998]. The native *E.coli* CPSase is a heterodimer composed of a small subunit of 41,270 Da and a large subunit of 117,710 Da, encoded by carA and carB genes respectively. The small subunit catalyzes the hydrolysis of glutamine and is responsible for the transfer of $NH_3$ to the large subunit, where the CP synthesis actually takes place. The large subunit contains the binding sites for the substrates bicarbonate, ammonia, two separate sites for Mg-ATP and a 18 kDa carboxyterminal region which constitutes the regulatory domain [Rubio V., et al., *Biochemistry*, vol. 30, p. 1068–1075, 1991; Cervera J., et al., *Biochemistry*, vol. 35, p. 7247–7255, 1996]. Further, it is suggested that the large subunit has an activity to catalyze solely a synthetic reaction of carbamoylphosphate (Stephen D. Rubino et al., *J. Biol. Chem.*, 206, 4382–4386, 1987).

The crystal structure of an allosterically activated form of CPSase has recently been described [Thoden J., et al., *Biochemistry*, vol. 36, p. 6305–6316, 1997; Thoden J., et al., *Acta Crystallogr. Sec. D.*, vol. 55, p. 8–24, 1999]. The first three distinct domains in the large subunit labeled as A, B, C are very similar in terms of structure, but the fourth one is entirely different. The D domain (residues 937–1073) is responsible for the binding and allosteric regulation by effectors: IMP, UMP and ornitine. Also it was shown, that two residues, serine 948 and threonine 1042, appear to be crucial for allosteric regulation of CPSase [Delannay S., et al., *J. Mol. Biol.*, vol. 286, p. 1217–1228, 1999]. When serine 948 is replaced with phenylalanine, the enzyme becomes insensitive to UMP and IMP, but still activated by ornitine, although to a reduced extent. The enzyme with T1042I mutation displays a greatly reduced activation by ornitine.

As a rule, the feed back resistance (fbr) phenotype of enzyme arises as a result of the replacing the amino acid residue with another in a single or in a few sites of amino acid sequence and these replacements lead to reducing the activity of enzyme. For example, the replacing of natural Met-256 with each of 19 other amino acid residues in *E.coli* serine acetyltransferase (SAT) (cysE gene) leads in most cases to fbr phenotype but the mutant SAT proteins do not restore the level of activity of natural SAT [Nakamori S. et al. AEM, vol. 64, p. 1607–1611, 1998]. So, the disadvantage of the mutant enzymes obtained by these methods is the reduced activity of mutant enzymes in comparison with the wild type enzymes.

SUMMARY OF THE INVENTION

The present invention is concerning the construction of feedback resistant and high active enzymes playing a key role in biosynthesis of pyrimidines and arginine or citrulline in *E.coli*.

In the present invention the novel procedure for synthesizing a large set of mutant carB genes using the full randomization of carB gene fragment is proposed. The simultaneous substitutions of some amino acid residues in fragment of amino acid sequence, in which the fbr mutation can be localized, can produce mutant proteins with restored level of activity close to the natural due to more correct accordance of three dimension structure of enzyme. Thus the present invention described below has been accomplished. That is the present invention provides:

(1) A large subunit of the carbamoylphosphate synthetase wherein the amino acid sequence corresponding to the positions from 947 to 951 of SEQ ID NO: 20 is replaced with any one of amino acid sequences of SEQ ID NOS: 1 to 9, and feedback inhibition by uridine 5'-monophosphate is desensitized;

(2) The large subunit of the carbamoylphosphate synthetase according to (1), wherein the carbamoylphosphate synthetase is that of *Escherichia coli*.

(3) The large subunit of the carbamoylphosphate synthetase according to (1), wherein the amino acid sequence of the positions from 947 to 951 of SEQ ID NO: 20 is replaced with any one of amino acid sequences of SEQ ID NOS: 1 to 9, and feedback inhibition by uridine 5'-monophosphate is desensitized;

(4) The large subunit of the carbamoylphosphate synthetase according to (1), which includes deletion, substitution, insertion, or addition of one or several amino acids at one or a plurality of positions other than the positions from 947 to 951, wherein feedback inhibition by uridine 5'-monophosphate is desensitized;
(5) A carbamoylphosphate synthetase which comprises the large subunit of the carbamoylphosphate synthetase according to any one of (1) to (4);
(6) A DNA coding for the carbamoylphosphate synthetase according to any one of (1) to (4), wherein feedback inhibition by uridine 5'-monophosphate is desensitized;
(7) A DNA coding the large subunit of carbamoylphosphate synthetase wherein feedback inhibition by uridine 5'-monophosphate is desensitized according to any one of (1) to (4), and a small subunit of carbamoylphosphate synthetase of *Escherichia coli*.;
(8) A bacterium belonging to the genus *Escherichia*, which harbors the DNA according to (6) or (7);
(9) The bacterium according to (8), which has an ability to produce a compound selected from the group consisting of L-arginine, citrulline and pyrimidine derivatives;
(10) The bacterium according to (9), wherein the pyrimidine derivatives are orotic acid, uridine, UMP, cytidine and CMP;
(11) A method for producing the compound which is selected from the group consisting of L-arginine, citrulline and pyrimidine derivatives, which method comprises the steps of cultivating the bacterium according to any of (8) to (10) in a medium to produce and accumulate the compound in the medium and collecting compound from the medium; and
(12) The method as defined in (11), wherein the pyrimidine derivatives are orotic acid, uridine, UMP, cytidine and CMP.

In the present invention, the term "CPSase activity" means activity to catalyze the reaction of the complex synthesis of carbamoylphosphate from bicarbonate, glutamine and two molecules of Mg-ATP. The "CPSase" of the present invention may be a single polypeptide consisting of the large subunit, or may be a heterodimer comprising the large subunit and the small subunit, provided that the CPSase has the CPSase activity. In the present application, the large subunit and the heterodimer as mentioned above may be generically referred to as "CPSase". A DNA encoding the large subunit and the small subunit may be referred to as "carAB".

The CPSase having any of fbr mutation as described above may be referred to as "the mutant CPSase", a DNA coding for the mutant CPSase may be referred to as "the mutant carB genes" or "the mutant carAB genes" according to the embodiment, and a CPSase without the mutation may be referred to as "a wild type CPSase".

Hereafter, the present invention will be explained in detail.

<1> Mutant CPSase and Mutant carB Gene

Subsequent selection and screening of recombinant clones carrying mutant carB genes cloned as carAB operon into expression vector allows to choose the fbr variants of mutant CPSase with different level of its biological activity.

According to the data obtained by S. Delannay et al. (Delannay S., et al., J. Mol. Biol., v. 286, 1217–1228, 1999) the mutant (S948F) of carbamoylphosphate synthase of *E.coli* is insensitive to UMP. Based on these data, the region including position 948 in CPSase was selected for the target of modification.

The mutant CPSase and the mutant carB gene are obtained by randomized fragment-directed mutagenesis. To obtain the numerous mutations in carB gene, the randomization of 15-nucleotide fragment of carB gene which codes for the region from Leu947 to Glu951 residues in the amino acid sequence SEQ ID NO: 20 is carried out (see below).

The randomized 15-nucleotide fragment gives $4^{12}$ or near $1.5 \times 10^7$ different DNA sequences which can code for $4 \times 10^5$ different amino acid residues in the 5-mer peptide. The likelihood of in frame non-introducing the stop codons in these sequences is about 0.95 or 95%. So, the randomization of the carB gene fragment coding for the peptide from 947-th to 951-th amino acid residues must give approximately $4 \times 10^5$ different amino acid sequences with diversity in this peptide fragment of CPSase structure. Subsequent selection and screening of recombinant clones carrying mutant carB genes cloned into expression vector allows to choose the fbr variants of mutant CPSases with different level of its biological activity.

The amino acid sequences of the mutant CPSase suitable for fbr phenotype of CPSase are defined by the present invention. Therefore, the mutant CPSase can be obtained based on the sequences by introducing mutations into a wild type carB gene using ordinary methods. As a wild type carB gene, the carB gene of *E. coli* can be mentioned (nucleotide numbers 10158 to 13379 in the sequence of GenBank Accession AE000113 U00096: SEQ ID NO: 19). The carA gene corresponds to nucleotide numbers 8992 to 10140 in the sequence of GenBank Accession U00096.

In the case that the carB gene is used for a material to obtain a DNA encoding the mutant CPSase, the mutant carB gene encoding the large subunit of the mutant CPSase. In the case that the carAB genes are used for the material, the mutant carAB gene encoding the large subunit of the mutant CPSase together with the small subunit.

The amino acid sequence of positions from 947 to 951 in the mutant CPSase of the present invention is any one of the sequence of SEQ ID NOS: 1 to 9. The corresponding amino acid sequence of known fbr CPSase, in which Ser at a position 948 is replaced with Phe, and the wild type CPSase of *E. coli* are illustrated in Table 1. Examples of nucleotide sequence encoding these amino acid sequences are also shown in Table 1.

TABLE 1

| No of clone | Sequence of randomized region of CarB protein (947→951 a.a.) | DNA sequence of SEQ randomized ID fragment of carB NO: gene (5'→3') | SEQ ID NO: |
|---|---|---|---|
| Wt | -Leu-Ser-Val-Arg-Glu- | 28 CTTTCCGTGCGCGAA | 30 |
| 6 (single mutation) | -Leu-*Phe*-Val-Arg-Glu- | 29 CTTT*T*CGTGCGCGAA | 31 |
| 10 | -Pro-Leu-Arg-Glu-Gly- | 1 CCTCTCCGTGAGGGT | 10 |
| 12 | -Ala-Val-Ala-Leu-Lys- | 2 GCTGTCGCTTTGAAA | 11 |
| 13 | -Gly-Val-Phe-Leu-Met- | 3 GGTGTCTTCCTAATG | 12 |
| 27 | -Phe-Phe-Cys-Phe-Gly- | 4 TTTTTCTGTTTTGGG | 13 |
| 31 | -Pro-Thr-Gly-Arg-Arg- | 5 CCTACCGGTAGGAGA | 14 |
| 33 | -Phe-Ala-Cys-Gly-Val- | 6 TTCGCCTGTGGGGTG | 15 |
| 34 | -Val-Phe-Gly-Ser-Ser- | 7 GTTTTCGGTAGTAGT | 16 |
| 36 | -Ala-Ser-Gly-Val-Glu- | 8 GCTTCCGGCGTTGAG | 17 |
| 37 | -Ala-Phe-Cys-Gly-Val- | 9 GCCTTCTGTGGGGTG | 18 |

The mutant CPSase may include deletion, substitution, insertion, or addition of one or several amino acids at one or a plurality of positions other than 947th to 951st. provided that the CPSase activity is not deteriorated. The number of "several" amino acids differs depending on the position or the type of amino acid residues in the three dimensional structure of the protein. This is because of the following reason. That is, some amino acids have high homology to one another and the difference in such an amino acid does not greatly affect the three dimensional structure of the protein. Therefore, the mutant CPSase of the present invention may be one which has homology of not less than 30 to 50%, preferably 50 to 70% with respect to the entire amino acid residues for constituting CPSase, and which has the fbr CPSase activity. The mutant CPSase desirably maintain the CPSase activity of not less than 25%, preferably not less than 30%, more preferably not less than 40% of the activity of the wild type CPSase in the presence of uridine 5'-monophosphate.

In the present invention, "amino acid sequence corresponding to the sequence of positions from 947 to 951" means an amino acid sequence corresponding to the amino acid sequence of positions from 947 to 951 in the amino acid sequence of SEQ ID NO: 20. A position of amino acid residue may change. For example, if an amino acid residue is inserted at N-terminus portion, the amino acid residue inherently locates at the position 947 becomes position 948. In such a case, the amino acid residue corresponding to the original position 947 is designated as the amino acid residue at the position 947 in the present invention.

The phrase "feedback inhibition by uridine 5'-monophosphate is desensitized" means that the degree of the feedback inhibition is lowered. The lowering of the degree of feedback inhibition can be determined by measuring the lowering of the CPSase activity in the presence of uridine 5'-monophosphate and by comparing it with that of protein having the amino acid sequence of SEQ ID NO: 20. Further, the phrase "feedback inhibition by uridine 5'-monophosphate is desensitized" means that substantial desensitization of inhibition is sufficient, and complete desensitization is not necessary. Concretely, it is desirable that the ratio of the activity of the mutant CPSase in the presence of 10 mM uridine 5'-monophosphate to the activity in the absence of uridine 5'-monophosphate is not less than 50%, preferably not less than 70%, more preferably not less than 90%, when 5 mM glutamine is used for a substrate.

The DNA, which codes for the substantially same protein as the mutant CPSase described above, may be obtained, for example, by modifying the nucleotide sequence, for example, by means of the site-directed mutagenesis method so that one or more amino acid residues at a specified site involve deletion, substitution, insertion, or addition. DNA modified as described above may be obtained by the conventionally known mutation treatment. The mutation treatment includes a method for treating a DNA containing the mutant carB gene in vitro, for example, with hydroxylamine, and a method for treating a microorganism, for example, a bacterium, belonging to the genus *Escherichia* harboring the mutant carB gene with ultraviolet irradiation or a mutating agent such as N-methyl-N'-nitro-N-nitrosoquanidine (NTG) and nitrous acid usually used for the such treatment.

The substitution, deletion, insertion, or addition of nucleotide as described above also includes mutation, which naturally occurs (mutant or variant), for example, on the basis of the individual difference or the difference in species or genus of bacterium, which harbors CPSase.

The DNA, which codes for substantially the same protein as the mutant CPSase, can be obtained by isolating a DNA which hybridizes with DNA having known carB gene sequence or part of it as a probe under stringent conditions, and which codes for a protein having the CPSase activity, from a cell harboring the mutant CPSase which is subjected to mutation treatment.

The term "stringent conditions" referred to herein means a condition under which so-called specific hybrid is formed, and non-specific hybrid is not formed. It is difficult to express this condition precisely by using any numerical value. However, for example, the stringent conditions include a condition under which DNAs having high homology, for example, DNAs having homology of not less than 50% with each other are hybridized, and DNAs having homology lower than the above with each other are not hybridized. Alternatively, the stringent condition is exemplified by a condition under which DNA's are hybridized with each other at a salt concentration corresponding to an ordinary condition of washing in Southern hybridization, i.g., 60° C., 1×SSC, 0.1% SDS, preferably 0.1×SSC, 0.1% SDS.

The gene, which is hybridizable under the condition as described above, includes those having a stop codon generated within a coding region of the gene, and those having no activity due to mutation of active center. However, such inconveniences can be easily removed by ligating the gene with a commercially available expression vector, and investigating CPSase activity of expressed protein.

When CPSase of the present invention is a heterodimer comprising the mutant large subunit and the small subunit, the small subunit is exemplified by a small subunit of a wild type CPSase of *Escherichia coli*.

In the present invention, the small subunit may include deletion, substitution, insertion, or addition of one or several amino acids at one or a plurality of positions, provided that it shows the CPSase activity together with the large subunit. The meaning of the term "several" is the same as described above for the large subunit.

As the DNA encoding the substantially same polypeptide as the small subunit described above, a DNA which is hybridizable to DNA containing carA or a part thereof under the stringent conditions can be mentioned. The meaning of the term "stringent conditions" is the same as described above.

<2> Bacterium Belonging to the Genus *Escherichia* of the Present Invention.

The bacterium belonging to the genus *Escherichia* of the present invention is a bacterium belonging to the genus *Escherichia* to which the mutant carB gene described above is introduced. A bacterium belonging to the genus *Escherichia* is exemplified by *E. coli*. The mutant carB gene can be introduced by, for example, transformation of a bacterium belonging to the genus *Escherichia* with a recombinant DNA comprising a vector which functions in a bacterium belonging to the genus *Escherichia* and the mutant carB gene. The mutant carB gene can be also introduced by substitution of carB gene on a chromosome with the mutant carB gene.

Vector using for introduction of the mutant carB gene is exemplified by plasmid vectors such as pBR322, pMW118, pUC19 or the like, phage vectors such as 11059, 1BF101, M13mp9 or the like and transposon such as Mu, Tn10, Tn5 or the like.

The introduction of a DNA into a bacterium belonging to the genus *Escherichia* can be performed, for example, by a method of D. A. Morrison (Methods in Enzymology, 68, 326 (1979)) or a method in which recipient bacterial cell are treated with calcium chloride to increase permeability of DNA (Mandel, M., and Higa, A., J. Mol. Biol., 53, 159, (1970)) and the like.

A produced amount of compound derived from carbamoylphosphate, such as L-arginine, citrulline and pyrimidine derivatives, can be increased by introduction of the mutant carB gene into producing bacterium belonging to the genus *Escherichia* as described above. Besides, an ability to produce compounds, such as L-arginine, citrulline and pyrimidine derivatives, may be imparted to a bacterium to which the mutant carB gene is introduced previously. The pyrimidine derivatives above include orotic acid, uridine, UMP, cytidine and CMP.

As the bacteria belonging to the genus *Escherichia* which have an activity to produce L-arginine are exemplified by *E. coli* strains AJ11531 and AF11538 (JP56106598A2), AJ11593 (FERM P-5616) and AJ11594 (FERM P-5617) (Japanese Patent Laid-open No. 57-5693), VKPM B-7925 (Russian Patent Application No. 2000117677). The strain VKPM B-7925 has been deposited in the Russian National Collection for Industrial Microorganisms (VKPM) since Apr. 10, 2000.

L-citrulline producing bacteria belonging to the genus *Escherichia*, orotate producing bacteria belonging to the genus *Escherichia* and uridine 5'-monophosphate (UMP) producing bacteria belonging to the genus *Escherichia* are not known at present.

As the bacteria belonging to the genus *Bacillus* which have an activity to produce L-citrulline are exemplified by *B. subtilis* strains K-X-1 A-1 (ATCC No 15561) and K-X-1 A-9 (ATCC No 15562) (U.S. Pat. No. 3,282,794), *Bacillus* sp. strain cit-70 (Japanese Laid-open patent application No. 08-089269). The bacteria belonging to the genus *Brevibacterium*, which have an activity to produce L-citrulline, are exemplified by *Brevibacterium flavum* strains AJ3408 (FERM P-1645) (U.S. Pat. No. 5,164,307) and AJ11677 (Japanese Laid-open patent application No. 57-163488). The bacterium belonging to the genus *Corynebacterium*, which has an activity to produce L-citrulline, is exemplified by *Corynebacterium glutamicum* strain AJ11588 (FERM P-5643) (U.S. Pat. No. 5,164,307).

As the bacterium belonging to the genus *Bacillus* which has an activity to produce orotic acid is exemplified by *B. subtilis* strain FERM P-11402, deficient in orotate phosphoribosyltransferase (Japanese Laid-open patent application No. 04-004891). The bacteria belonging to the genus *Corynebacterium* which have an activity to produce UMP are exemplified by *Corynebacterium glutamicum* strains T-26 (FERM BP-1487), resistant to 5-fluorouracyl, T-29 (FERM BP-1488), resistant to 5-fluorouracyl and trimethoprim, and T-30 (FERM BP-1489), resistant to 5-fluorouracyl and sulfaguanidine (European patent EP0312912).

The bacteria belonging to the genus *Corynebacterium* which have an activity to produce UMP are exemplified by *Corynebacterium ammoniagenes* strains LK 40-2 (VKPM B-7811), LK 75-15 (VKPM B-7812), and LK 75-66 (VKPM B-7813) (Russian patent application No. 99122774).

<3> Method for Producing L-arginine, Citrulline and Pyrimidine Derivatives.

Compounds, such as L-arginine, citrulline and pyrimidine derivatives, can be efficiently produced by cultivating the bacterium to which the mutant carB gene is introduced and which has an ability to produce said compounds in a culture medium, producing and accumulating said compounds in the medium, and collecting them from the medium. The pyrimidine derivatives above include orotic acid, uridine, UMP, cytidine and CMP. In the method of present invention, the cultivation of the bacterium belonging to the genus *Escherichia*, the collection and purification of compounds from the liquid medium may be performed in a manner similar to those of the conventional method for producing L-arginine by fermentation using a bacterium. A medium used in cultivation may be either a synthetic medium or a natural medium, so long as the medium includes a carbon and a nitrogen source and minerals and, if necessary, nutrients the bacterium used requires for growth in appropriate amount. The carbon source may include various carbohydrates such as glucose and sucrose, and various organic acids, depending on assimilatory ability of the used bacterium. Alcohol including ethanol and glycerol may be used. As the nitrogen source, ammonia, various ammonium salts as ammonium sulfate, other nitrogen compounds such as amines, a natural nitrogen source such as peptone, soybean hydrolyzate and digested fermentative microbe may be used. As minerals, monopotassium phosphate, magnesium sulfate, sodium chloride, ferrous sulfate, manganese sulfate, calcium carbonate may be used.

The cultivation is preferably the one under an aerobic condition such as a shaking, and aeration and stirring culture. The cultivation is usually performed at a temperature between 20 and 40° C., preferably 30 and 38° C. The cultivation is usually performed at a pH between 5 and 9, preferably between 6.5 and 7.2. The pH of the culture medium can be adjusted with ammonia, calcium carbonate, various acids, various bases, and buffers. Usually, a 1 to 3-day cultivation leads to the accumulation of the compounds in the medium.

The isolation of the compounds can be performed by removing solids such as cells from the medium by centrifugation or membrane filtration after cultivation, and then collecting and purifying such compounds by ion exchange, concentration and crystalline fraction methods and the like.

BEST MODE FOR CARRYING OUT THE INVENTION

Figure 1:
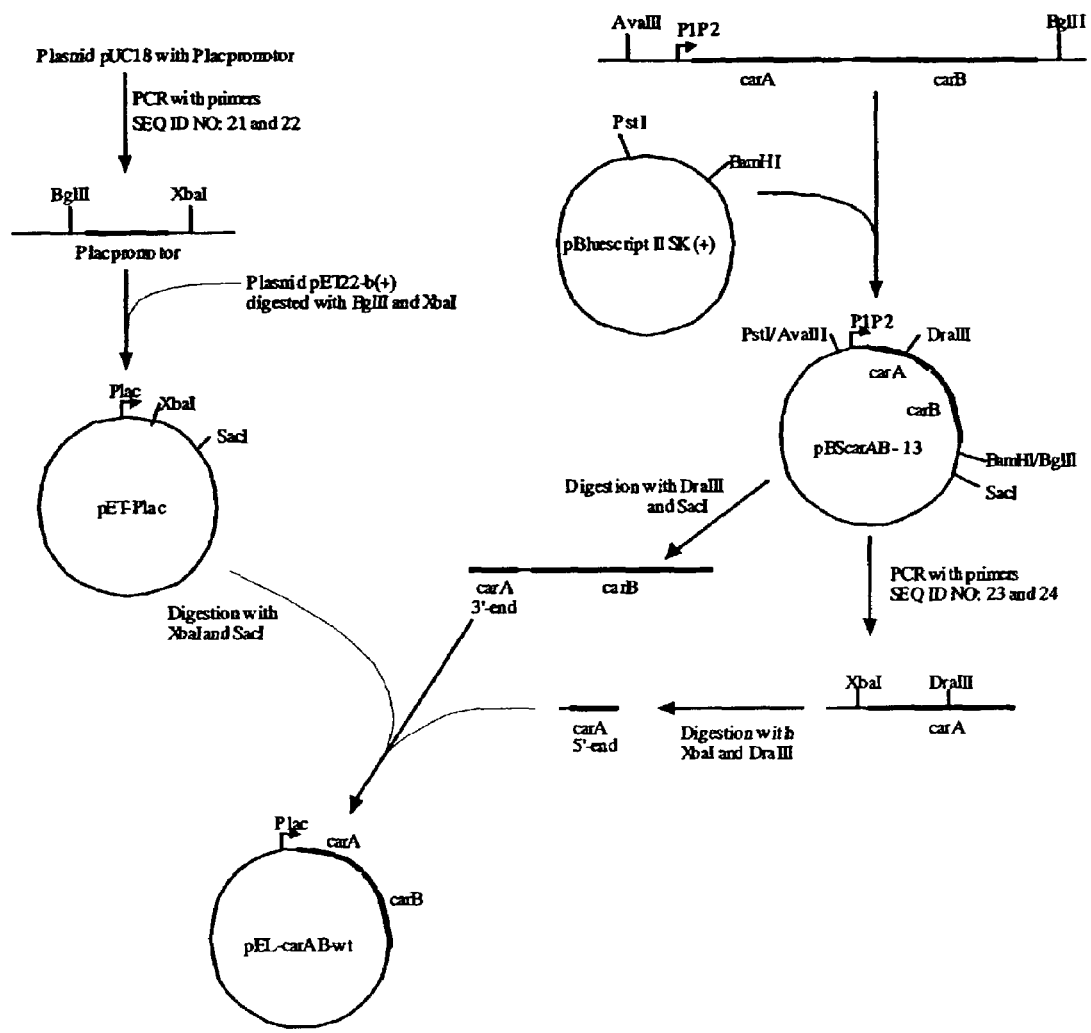
FIG. 1 shows scheme of construction the plasmid pEL-carAB-wt.
Figure 2:
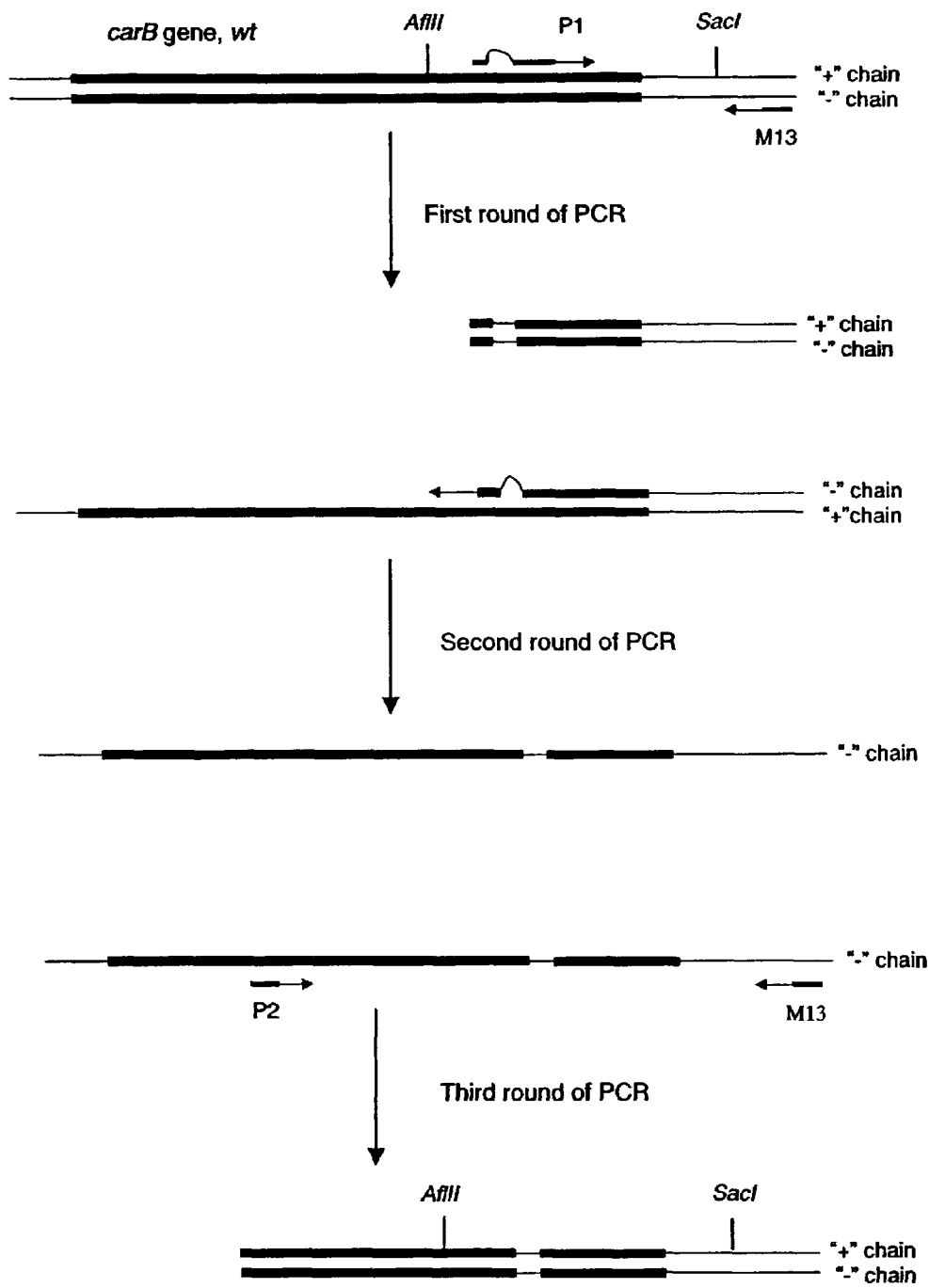
FIG. 2 shows scheme of construction the pool of mutant carB genes.

The present invention will be specifically explained with reference to the following examples.

EXAMPLE 1

The plasmid pBScarAB-13 carrying wild type carAB genes from *E.coli* was constructed by cloning the AvaIII-BglII DNA fragment (4911 bp) from *E.coli* chromosome to pBluescript II SK(+) vector (Fermentas, Lithuania) previously digested by BamHI and PstI.

The plasmid pET22-b(+) (Novagen, USA) was modified to substitute the T7 promoter by lac promoter. The lac promoter was obtained by PCR amplification using plasmid pUC18 as a template and the oligonucleotides 5'-accagatct-gcgggcagtgagcgcaacgc-3' (SEQ ID NO: 21) and 5'-gtttcta-gatcctgtgtgaaattgttatccgc-3' (SEQ ID NO: 22) as a primers. The resulted fragment (0.14 kb) carrying the lac promoter was digested by restrictases BglII and XbaI and cloned into pET22-b(+) vector previously digested by the same restrictases. The resulted plasmid pET-Plac was used for cloning the carAB genes without promoter from plasmid pBScarAB-13.

The 5'-end of carA gene (1.18 kb) was obtained by PCR amplification using pBScarAB-13 as a template and oligonucleotides 5'-cctctagaaataaagtgagtgaatattc-3' (SEQ ID NO: 23) and 5'-cttagcggttttacggtactgc-3' (SEQ ID NO: 24) as a primers. The resulted fragment was digested by XbaI and DraIII and XbaI-DraIII fragment (0.61 kb) carrying 5'-end sequence of carA gene was purified by agarose electrophoresis. The mixture of this fragment, the DraIII-SacI fragment from plasmid pBScarAB-13 (carrying sequences of 3'-end of carA gene and carB gene) and vector pET-Plac/XbaI-SacI were ligated and transformed into E.coli TG1 cells. The recombinant plasmid pEL-carAB-wt obtained carried sequence of wild type carAB operon under control of lac promoter.

The TaKaRa La DNA Polymerase used for PCR amplification was obtained from Takara Shuzo Co. (Japan) and was used under the conditions recommended by the supplier.

<1> The Randomized Fragment-directed Mutagenesis

The plasmid pBScarAB-13 was used as the template, the sense primer P1: 5'-ggtcgtgcgctgNN(T/C)N(T/C)CNN(T/C)NNN(G/A)NNggcgataaagaacgcgtggtg-3' (SEQ ID NO: 25) (48 bases) is designed based on the nucleotide sequence of carB gene and the standard M13 direct sequence primer is used as a antisense primer. The fixed 12-nucleotide 5'-end and fixed 21-nucleotide 3'-end regions of primer P1 are homologous to the sequence of carB gene downstream Glu951 codon and upstream Leu947 codon, respectively.

The 0.75 kbp DNA fragment (3'-end of carB gene) was synthesized during first round of PCR (15 cycles) using the primer P1 with randomized 15 nucleotide region. The first round of PCR was performed as follows. 100 ng of plasmid pBScarAB-13 were added as a template to PCR solution (50 µl) containing each of the two primers at a concentration of 10 pmol. Fifteen PCR cycles (94° C. for 15 sec, 52° C. for 20 sec, 72° C. for 1 min) was carried out with a model 2400 DNA thermal cycler (Perkin-Elmer Co., Foster City, Calif.)

At the second round of amplification the next fifteen cycles (94° C. for 1 min, 35° C. for 1 min, 72° C. for 2 min) was carried out in which the (−) chain of this fragment is functioning as a "primer" for extension it to get the full gene sequence.

At the third round, the 10 µl aliquot of the reaction mixture was added to a fresh 90 µl reaction mixture containing 100 pmol of the sense primer: standard M13 direct sequence primer and primer P2: 5'-ccacttcctcgatgacgcgg-3' (SEQ ID NO: 26) as antisense, and additional fifteen cycles (94° C. for 0.5 min, 55° C. for 20 sec. 72° C. for 2 min) was performed.

The 1.32 kb DNA fragment coding the pool of mutant variants of 3'-end fragment of carB gene was purified by agarose gel electrophoresis, then was digested with AflII and SacI, and further was ligated to the pEL-carAB-wt vector previously digested by the same restrictases to obtain pEL-carAB-NN.

About 150 ng of DNA ligated was used for transformation of E.coli TG1 (supE hsdΔ5 thi Δ(lac-proAB) F'[traD36 proAB+ lacI$^q$ lacZΔM15]) (J. Sambrook et al., Molecular Cloning, 1989) recipient cells in subsequent experiments to give about 2000 recombinant clones in each case. The pool of recombinant plasmids (pEL-carAB-NN) was purified and transformed into E.coli cells VKPM B-6969 (carB::Tn10), which were used to select the recombinant plasmids pEL-carAB-NN carrying carAB genes encoding active CarAB enzymes.

<2> The Site-directed Mutagenesis

For introducing the single mutation Ser948Phe PCR was performed using the plasmid pBScarAB-13 as the template, the sense primer 5'-cgtgcgctgcttttcgtgcgcgaaggcgataaag-3' (34 bases) (SEQ ID NO: 27) designed based on the nucleotide sequence of carB gene and the standard M13 direct sequence primer as a antisense primer. The PCR amplification and cloning of the fragments was carried out as described above.

The 1.32 kbp DNA fragment coding the 3'-end fragment of carB gene with single mutation was purified by agarose gel electrophoresis, was digested with AflII and SacI. and then was ligated to the pEL-carAB-wt vector previously digested with the same restrictases.

About 100 ng of resulted DNA plasmid was used for transformation of E.coli cells VKPM B-6969 and the recombinant plasmid pEL-carAB-6 carrying active CarAB enzymes with single substitution Ser948Phe was selected.

EXAMPLE 2

Isolation of New carB Mutants and Effect of Amino Acid Substitutions in CPSase on Catalytic Properties At first, the CarAB activity and its feed back resistance to UMP were evaluated in reactions of biosynthesis of the citrulline from ornithine catalyzed by CarAB and ArgI (ornitine carbamoyltransferase) enzymes in forty recombinant B-6969(pEL-carAB-NN) clones.

The scheme of reaction is following:

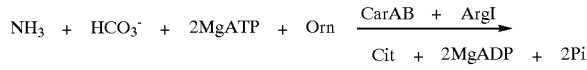

$$NH_3 + HCO_3^- + 2MgATP + Orn \xrightarrow{CarAB + ArgI} Cit + 2MgADP + 2Pi$$

In this reaction carbamoylphosphate synthetase uses free $NH_4^+$ as substrate.

The protein extracts from forty B-6969(pEL-carAB-NN) strains and TG1(pUC18-argI) cells were prepared from crude cellular extracts of sonicated cells by precipitation with $(NH_4)_2SO_4$ (75% of saturation). The protein precipitates were solubilized in buffer of following composition: Tris-HCl (50 mM), pH 7.5, 2-mercaptoethanol (2 mM).

The test-system included the protein extracts from strains B-6969(pEL-carAB-NN) and TG1(pUC18-argI) and following reagents: ATP (8 mM), $MgSO_4$ (8 mM), $(NH_4)_2SO_4$ (200 mM), $Na_2CO_3$ (8 mM) and ornitine (1 mM), (pH 7.5). Content of ornitine and citrulline in reaction mixtures was analyzed by TLC using the liquid phase of following composition: isopropanol/ethyl acetate/ammonium hydroxide/$H_2O$=40/20/13/27 (v/v).

The 9 clones which expressed the active and feed-back resistant to UMP mutant CPSases and one clone which expressed mutant CPSase with single substitution Ser948Phe were used for measuring the mutant enzymes activity.

The plasmids from said 10 clones were purified and sequences of randomized fragments of carB genes were determined using dideoxy chain termination method (table 1).

Then, the protein extracts from these 9 clones B-6969 (pEL-carAB-NN) and one clone B-6969(pEL-carAB-6) were used to evaluate the activity and fbr of mutant CPSases in reaction of carbamoylphosphate (CP) synthesis from glutamine or ammonia.

The crude cellular extracts from cells were prepared by sonication of 20 mg wet cells pellet suspended in 0,5 ml of buffer A (200 mM $K_2HPO_4/KH_2PO_4$, pH 8.0, 1 mM EDTA, 1 mM PMSF, 1 mM DTT) and treated with solid ammonium sulfate to achieve 65% of saturation. After incubation for 10 min at 4° C., the suspensions were centrifuged at 13,000 rpm for 10 min and the precipitates were dissolved in 1 ml of buffer B (20 mM $K_2HPO_4/KH_2PO_4$, pH 8.0, 50 mM KCl, 1 mM PMSF, 1 mM DTT). The aliquots of obtained protein extracts were used to evaluate the CPSase activity. The schemes of reaction were following:

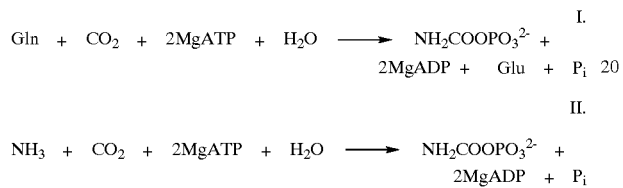

I. $Gln + CO_2 + 2MgATP + H_2O \longrightarrow NH_2COOPO_3^{2-} + 2MgADP + Glu + P_i$ II. $NH_3 + CO_2 + 2MgATP + H_2O \longrightarrow NH_2COOPO_3^{2-} + 2MgADP + P_i$ The 50 μl of each reaction mixture included:

reaction I—20 mM tris-HCl, pH 8.0, 100 mM KCl, 5 mM $Na_2CO_3$, 10 mM ATP, 10 mM $MgCl_2$, 5 mM glutamine, 10 μl of protein extract;

reaction II—20 mM tris-HCl, pH 8.0, 100 mM KCl, 5 mM $Na_2Co_3$, 10 mM ATP, 10 mM $MgCl_2$, 200 mM $(NH_4)_2SO_4$, 10 μl of protein extract.

Also, the series of reaction I were carried out in the presence of 10 mM UTP to estimate the level of feed back inhibition of CPSases.

After incubation for 10 min at 37° C. reactions were stopped by addition of equal volume of EtOH, cooled at −20° C. for 10 min and centrifuged at 13,000 rpm for 1 min at room temperature. Supernatants were cooled at −20° C.

The CP content in reaction mixtures was analyzed by capillary zone electrophoresis. The separation was performed on a Quanta 4000E Capillary Electrophoresis System ("Waters", USA) with UV indirect detection at 254 nm. The injection was performed by hydrostatic for 25 s. The separation was carried out with an uncoated fused-silica capillary (75u I.D.* 60 cm, effective length 53 cm) and was operated at −25 kV potential. Temperature was maintained at 20° C. The separation buffer consisted of 50 mM Tris base, 25 mM benzoic acid (for indirect detection), pH 8.5, 0.25 mM TTAB (tetradecyl-trimethyl-ammonium bromide) (for reversion of electroosmotic flow).

The data of the measured activity and fbr of mutant CPSases in reaction of CP synthesis are shown in the Table 2.

TABLE 2

The activity of mutant CPSases

Activity, (CP, nmol/mg × min)

| No of clone | Substrate: 5 mM Gln | Substrate: 200 mM $(NH_4)_2SO_4$ | Substrate: 5 mM Gln; Allosteric effector: 10 mM UMP |
|---|---|---|---|
| Wt | 1350 | 425 | 170 |
| 6 | 320 | 220 | 320 |
| 10 | 690 | 225 | 625 |

TABLE 2-continued

The activity of mutant CPSases

Activity, (CP, nmol/mg × min)

| No of clone | Substrate: 5 mM Gln | Substrate: 200 mM $(NH_4)_2SO_4$ | Substrate: 5 mM Gln; Allosteric effector: 10 mM UMP |
|---|---|---|---|
| 12 | 540 | 95 | 540 |
| 13 | 350 | 60 | 350 |
| 27 | 730 | 400 | 670 |
| 31 | 1120 | 375 | 810 |
| 33 | 510 | 150 | 510 |
| 34 | 765 | 345 | 765 |
| 36 | 390 | 90 | 390 |
| 37 | 475 | 205 | 475 |

So, the mutated CPSases are essentially insensitive to UMP but the single mutation significantly reduced the activity of enzyme. These results indicate that peptide fragment from 947 to 951 amino acid residues is responsible for the feedback inhibition of CPSase by UMP and for the level of catalytic efficiency of mutant CPSases as well.

The genes coding the wt CarAB and the mutant CarAB-34 were cloned into plasmid pMW119. For this purpose, the plasmids pEL-carAB-wt and pEL-carAB-34 were digested by restrictases SacI and XbaI (partial digestion was used because said plasmids carried two XbaI sites) and fragments coding carAB genes were cloned into pMW119 vector previously treated by the same restrictases. As a result, the low-copy number plasmids pMW119carAB-wt and pMW119carAB-34 carrying carAB genes under control of lac promoter were constructed.

EXAMPLE 3

Production of Orotic Acid Using the Strains Carrying Mutant carAB Genes

The strain 311 was derived from *E.coli* K12 having insertion of Tn 10 into the argA gene (VKPM B-3853) as a mutant strain resistant to 6-azauracil (1 mg/ml). The strain 311 has been deposited in the Russian National Collection of Industrial Microorganisms (VKPM) under the accession number: VKPM B-8085, since Mar. 5, 2001, and then the original deposit was converted to the international deposit on Jul. 17, 2002, according to the provisions of Budapest Treaty.

Strain 311 was transformed with plasmids pMW-carABwt and pMW-carAB-34 and production of orotic acid by resulted recombinant strains in the presence of different concentrations of uridine was tested.

The cultivation conditions in test-tube fermentation was as follows:

1/20 diluted overnight culture, 60 g/l glucose, 25 g/l ammonia sulfate, 2 g/l $KH_2PO_4$, 1 g/l $MgSO_4$, 0.1 mg/l thiamine, 5 g/l yeast extract Difco, 25 g/l chalk, per 1 liter of tap water (pH 7.2). Glucose and chalk were sterilized separately. 2 ml of the medium was placed into test-tubes, and the cultivation was carried out at 32° C. for 3 days with shaking. The level of orotic acid production was evaluated by HPLC (table 3).

TABLE 3

The level of orotic acid production in strains
311 (pMW119), 311 (pMW-CarAB-wt), 311 (pMW-CarAB-34)

| Strain | Uridine, 100 mg/l | | Uridine, 300 mg/l | | Uridine, 1000 mg/l | |
|---|---|---|---|---|---|---|
| | $A_{550}$, o.u. | Orotic acid biosynthesis, g/l | $A_{550}$, o.u. | Orotic acid biosynthesis, g/l | $A_{550}$, o.u. | Orotic acid biosynthesis, g/l |
| 311 (pMW119) | 13.1 | 0.12 | 13.8 | 0.11 | 9.0 | 0.01 |
| 311 (pMW-CarAB-wt) | 11.4 | 0.27 | 12.2 | 0.18 | 9.8 | 0.03 |
| 311 (pMW-CarAB-34) | 12.6 | 0.66 | 12.7 | 0.40 | 10.3 | 0.11 |

As is shown in the Table 3, the strain 311(pMW-CarAB-34) carrying mutant carAB gene produced more orotic acid compared to the parent strain 311(pMW119) and strain 311(pMW-CarAB-wt) carrying wild type carAB gene.

EXAMPLE 4

Production of Arginine and/or Citrulline Using the Strains Carrying Mutant carAB Genes The arginine producing strains 333 and 374 have been selected from the derivative of the strain E.coli 57 (VKPM B-7386) having insertion of transposone Tn 5 into the gene ilvA as mutants resistant to 6-azauracil (1 mg/ml). The strains 333 and 374 have been deposited in the Russian National Collection of Industrial Microorganisms (VKPM) under the accession numbers VKPM B-8084 and VKPM B-8086, respectively, since Mar. 5, 2001, and then the original deposit was converted to the international deposit on Jul. 17, 2002, according to the provisions of Budapest Treaty.

The strains 333 and 374 were transformed with plasmids pMW-carABwt and pMW-carAB-34 and production of Arg and Cit by these recombinant strains was tested.

The test-tube fermentation was performed the same manner as in Example 3.

The levels of Arg and/or Cit production by strains 333 (pMW-CarAB-wt) and 333(pMW-CarAB-34) in synthetic medium with 100 mg/l uridine are shown in the Table 4.

TABLE 4

The levels of Arg and/or Cit production in
strains 333(pMW-CarAB-wt) and 333(pMW-CarAB-34)

| Strain | Absorbance, $A_{560}$, u. | Level of Arg biosynthesis, g/l | Level of Cit biosynthesis, g/l | Level of Arg + Cit biosynthesis, g/l |
|---|---|---|---|---|
| 333(pMW-CarABwt) | 24.1 | 0.60 | 0.39 | 0.99 |
| 333(pMW-CarAB-34) | 20.5 | 1.01 | 0.51 | 1.52 |

The level of Cit production by strains 374(pMW-CarAB-wt) and 374(pMW-CarAB-34) in synthetic medium with 100 mg/l uridine are shown in the Table 5.

TABLE 5

The level of Cit production in
strains 374(pMW-CarAB-wt) and 374(pMW-CarAB-34)

| Strain | Absorbance, $A_{560}$, u. | Level of Cit biosynthesis, g/l |
|---|---|---|
| 374(pMW-CarABwt) | 22.3 | <0.01 |
| 374(pMW-CarAB-34) | 15.5 | 0.26 |

As is shown in the table 4, the strain 333(pMW-CarAB-34) carrying mutant carAB gene produced more Arg and Cit than the strains carrying wild type carAB gene. As is shown in the Table 5, the strain 374(pMW-CarAB-34) produced more Cit than the strains carrying wild type carAB gene.

---

What is claimed is:

1. A DNA coding for a mutant of a large subunit of a carbamoylphosphate synthetase, wherein said mutant has an amino acid sequence of a large subunit of carbamoylphosphate synthetase as defined in the following (A) or (B), whereby amino acid residues corresponding to positions 947 to 951 of SEQ ID NO:20 are replaced with any one of amino acid sequences of SEQ ID NOs:1 to 9, and is desensitized to feedback inhibition by uridine 5'-monophosphate:

(A) a protein having the amino acid sequence defined in SEQ ID NO:20; or (B) a protein that is encoded by a DNA which hybridizes with a DNA having the nucleotide sequence defined in SEQ ID NO:19 under stringent conditions, and has a carbamoylphosphate synthetase activity, wherein said stringent conditions entail a temperature of 60° C., a salt concentration of 0.1×SSC, and 0.1% SDS.

2. A DNA coding for a mutant of a large subunit of carbamoylphosphate synthetase, and a small subunit of carbamoylphosphate synthetase of *Escherichia coli*, wherein said mutant has an amino acid sequence of a large subunit of carbamoylphosphate synthetase as defined in the following (A) or (B), whereby amino acid residues corresponding to positions 947 to 951 of SEQ ID NO:20 are replaced with any one of amino acid sequences of SEQ ID NOs:1 to 9, and is desensitized to feedback inhibition by uridine 5'-monophosphate:

(A) a protein having the amino acid sequence defined in SEQ ID NO:20; or (B) a protein that is encoded by a DNA which hybridizes with a DNA having the nucleotide sequence defined in SEQ ID NO:19 under stringent conditions, and has a carbamoylphosphate synthetase activity, wherein said stringent conditions entail a temperature of 60° C., a salt concentration of 0.1×SSC, and 0.1% SDS.

3. A bacterium belonging to the genus *Escherichia*, which is transformed with the DNA according to claim 1.

4. The bacterium according to claim 3, which has an ability to produce a compound selected from the group consisting of L-arginine, citrulline and pyrimidine derivatives.

5. The bacterium according to claim 4, wherein the pyrimidine derivatives are orotic acid, uridine, uridine 5'-monophosphate, cytidine and cytidine 5'-monophosphate.

6. A bacterium belonging to the genus *Escherichia*, which is transformed with the DNA according to claim 2.

7. The bacterium according to claim 6, which has an ability to produce a compound selected from the group consisting of L-arginine, citrulline and pyrimidine derivatives.

8. The bacterium according to claim 7, wherein the pyrimidine derivatives are orotic acid, uridine, uridine 5'-monophosphate, cytidine and cytidine 5'-monophosphate.

9. A method for producing a compound selected from the group consisting of L-arginine, citrulline and pyrimidine derivatives, comprising cultivating the bacterium according to claim 3 in a medium to produce and accumulate the compound in the medium and collecting the compound from the medium.

10. The method according to claim 9, wherein the pyrimidine derivatives are orotic acid, uridine, uridine 5'-monophosphate, cytidine and cytidine 5'-monophosphate.

11. A method for producing the compound selected from the group consisting of L-arginine, citrulline and pyrimidine derivatives, comprising cultivating the bacterium according to claim 6 in a medium to produce and accumulate the compound in the medium and collecting the compound from the medium.

12. The method according to claim 11, wherein the pyrimidine derivatives are orotic acid, uridine, uridine 5'-monophosphate, cytidine and cytidine 5'-monophosphate.

* * * * *

SEQUENCE LISTING

<160> NUMBER OF SEQ ID NOS: 33

<210> SEQ ID NO 1
<211> LENGTH: 5
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 1

Pro Leu Arg Glu Gly
1               5

```
<210> SEQ ID NO 2
<211> LENGTH: 5
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 2

Ala Val Ala Leu Lys
1               5

<210> SEQ ID NO 3
<211> LENGTH: 5
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 3

Gly Val Phe Leu Met
1               5

<210> SEQ ID NO 4
<211> LENGTH: 5
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 4

Phe Phe Cys Phe Gly
1               5

<210> SEQ ID NO 5
<211> LENGTH: 5
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 5

Pro Thr Gly Arg Arg
1               5

<210> SEQ ID NO 6
<211> LENGTH: 5
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 6

Phe Ala Cys Gly Val
1               5

<210> SEQ ID NO 7
<211> LENGTH: 5
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 7

Val Phe Gly Ser Ser
1               5
```

```
<210> SEQ ID NO 8
<211> LENGTH: 5
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 8

Ala Ser Gly Val Glu
1               5

<210> SEQ ID NO 9
<211> LENGTH: 5
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 9

Ala Phe Cys Gly Val
1               5

<210> SEQ ID NO 10
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
cctctccgtg agggt                                                       15

<210> SEQ ID NO 11
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
gctgtcgctt tgaaa                                                       15

<210> SEQ ID NO 12
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
ggtgtcttcc taatg                                                       15

<210> SEQ ID NO 13
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
tttttctgtt ttggg                                                       15
```

```
<210> SEQ ID NO 14
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 14
cctaccggta ggaga                                                          15

<210> SEQ ID NO 15
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
ttcgcctgtg gggtg                                                          15

<210> SEQ ID NO 16
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 16
gttttcggta gtagt                                                          15

<210> SEQ ID NO 17
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 17
gcttccggcg ttgag                                                          15

<210> SEQ ID NO 18
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
gccttctgtg gggtg                                                          15

<210> SEQ ID NO 19
<211> LENGTH: 3222
<212> TYPE: DNA
<213> ORGANISM: Escherichia coli
<220> FEATURE:
<221> NAME/KEY: CDS
<222> LOCATION: (1)..(3222)
<223> OTHER INFORMATION:

<400> SEQUENCE: 19 atg cca aaa cgt aca gat ata aaa agt atc ctg att ctg ggt gcg ggc           48
Met Pro Lys Arg Thr Asp Ile Lys Ser Ile Leu Ile Leu Gly Ala Gly
1               5                   10                  15 ccg att gtt atc ggt cag gcg tgt gag ttt gac tac tct ggc gcg caa           96
Pro Ile Val Ile Gly Gln Ala Cys Glu Phe Asp Tyr Ser Gly Ala Gln
            20                  25                  30
```

```
gcg tgt aaa gcc ctg cgt gaa gag ggt tac cgc gtc att ctg gtg aac      144
Ala Cys Lys Ala Leu Arg Glu Glu Gly Tyr Arg Val Ile Leu Val Asn
        35                  40                  45 tcc aac ccg gcg acc atc atg acc gac ccg gaa atg gct gat gca acc      192
Ser Asn Pro Ala Thr Ile Met Thr Asp Pro Glu Met Ala Asp Ala Thr
 50                  55                  60 tac atc gag ccg att cac tgg gaa gtt gta cgc aag att att gaa aaa      240
Tyr Ile Glu Pro Ile His Trp Glu Val Val Arg Lys Ile Ile Glu Lys
65                  70                  75                  80 gag cgc ccg gac gcg gtg ctg cca acg atg ggc ggt cag acg gcg ctg      288
Glu Arg Pro Asp Ala Val Leu Pro Thr Met Gly Gly Gln Thr Ala Leu
                85                  90                  95 aac tgc gcg ctg gag ctg gaa cgt cag ggc gtg ttg gaa gag ttc ggt      336
Asn Cys Ala Leu Glu Leu Glu Arg Gln Gly Val Leu Glu Glu Phe Gly
            100                 105                 110 gtc acc atg att ggt gcc act gcc gat gcg att gat aaa gca gaa gac      384
Val Thr Met Ile Gly Ala Thr Ala Asp Ala Ile Asp Lys Ala Glu Asp
            115                 120                 125 cgc cgt cgt ttc gac gta gcg atg aag aaa att ggt ctg gaa acc gcg      432
Arg Arg Arg Phe Asp Val Ala Met Lys Lys Ile Gly Leu Glu Thr Ala
130                 135                 140 cgt tcc ggt atc gca cac acg atg gaa gaa gcg ctg gcg gtt gcc gct      480
Arg Ser Gly Ile Ala His Thr Met Glu Glu Ala Leu Ala Val Ala Ala
145                 150                 155                 160 gac gtg ggc ttc ccg tgc att att cgc cca tcc ttt acc atg ggc ggt      528
Asp Val Gly Phe Pro Cys Ile Ile Arg Pro Ser Phe Thr Met Gly Gly
                165                 170                 175 agc ggc ggc ggt atc gct tat aac cgt gaa gag ttt gaa gaa att tgc      576
Ser Gly Gly Gly Ile Ala Tyr Asn Arg Glu Glu Phe Glu Glu Ile Cys
                180                 185                 190 gcc cgc ggt ctg gat ctc tct ccg acc aaa gag ttg ctg att gat gag      624
Ala Arg Gly Leu Asp Leu Ser Pro Thr Lys Glu Leu Leu Ile Asp Glu
            195                 200                 205 tcg ctg atc ggc tgg aaa gag tac gag atg gaa gtg gtg cgt gat aaa      672
Ser Leu Ile Gly Trp Lys Glu Tyr Glu Met Glu Val Val Arg Asp Lys
210                 215                 220 aac gac aac tgc atc atc gtc tgc tct atc gaa aac ttc gat gcg atg      720
Asn Asp Asn Cys Ile Ile Val Cys Ser Ile Glu Asn Phe Asp Ala Met
225                 230                 235                 240 ggc atc cac acc ggt gac tcc atc act gtc gcg cca gcc caa acg ctg      768
Gly Ile His Thr Gly Asp Ser Ile Thr Val Ala Pro Ala Gln Thr Leu
                245                 250                 255 acc gac aaa gaa tat caa atc atg cgt aac gcc tcg atg gcg gtg ctg      816
Thr Asp Lys Glu Tyr Gln Ile Met Arg Asn Ala Ser Met Ala Val Leu
                260                 265                 270 cgt gaa atc ggc gtt gaa acc ggt ggt tcc aac gtt cag ttt gcg gtg      864
Arg Glu Ile Gly Val Glu Thr Gly Gly Ser Asn Val Gln Phe Ala Val
            275                 280                 285 aac ccg aaa aac ggt cgt ctg att gtt atc gaa atg aac cca cgc gtg      912
Asn Pro Lys Asn Gly Arg Leu Ile Val Ile Glu Met Asn Pro Arg Val
290                 295                 300 tcc cgt tct tcg gcg ctg gcg tcg aaa gcg acc ggt ttc ccg att gct      960
Ser Arg Ser Ser Ala Leu Ala Ser Lys Ala Thr Gly Phe Pro Ile Ala
305                 310                 315                 320 aaa gtg gcg gcg aaa ctg gcg gtg ggt tac acc ctc gac gaa ctg atg     1008
Lys Val Ala Ala Lys Leu Ala Val Gly Tyr Thr Leu Asp Glu Leu Met
                325                 330                 335 aac gac atc act ggc gga cgt act ccg gcc tcc ttc gag ccg tcc atc     1056
Asn Asp Ile Thr Gly Gly Arg Thr Pro Ala Ser Phe Glu Pro Ser Ile
            340                 345                 350
```

-continued

```
gac tat gtg gtt act aaa att cct cgc ttc aac ttc gaa aaa ttc gcc        1104
Asp Tyr Val Val Thr Lys Ile Pro Arg Phe Asn Phe Glu Lys Phe Ala
        355                 360                 365 ggt gct aac gac cgt ctg acc act cag atg aaa tcg gtt ggc gaa gtg        1152
Gly Ala Asn Asp Arg Leu Thr Thr Gln Met Lys Ser Val Gly Glu Val
370                 375                 380 atg gcg att ggt cgc acg cag cag gaa tcc ctg caa aaa gcg ctg cgc        1200
Met Ala Ile Gly Arg Thr Gln Gln Glu Ser Leu Gln Lys Ala Leu Arg
385                 390                 395                 400 ggc ctg gaa gtc ggt gcg act gga ttc gac ccg aaa gtg agc ctg gat        1248
Gly Leu Glu Val Gly Ala Thr Gly Phe Asp Pro Lys Val Ser Leu Asp
                405                 410                 415 gac ccg gaa gcg tta acc aaa atc cgt cgc gaa ctg aaa gac gca ggc        1296
Asp Pro Glu Ala Leu Thr Lys Ile Arg Arg Glu Leu Lys Asp Ala Gly
            420                 425                 430 gca gat cgt atc tgg tac atc gcc gat gcg ttc cgt gcg ggc ctg tct        1344
Ala Asp Arg Ile Trp Tyr Ile Ala Asp Ala Phe Arg Ala Gly Leu Ser
        435                 440                 445 gtg gac ggc gtc ttc aac ctg acc aac att gac cgc tgg ttc ctg gta        1392
Val Asp Gly Val Phe Asn Leu Thr Asn Ile Asp Arg Trp Phe Leu Val
450                 455                 460 cag att gaa gag ctg gtg cgt ctg gaa gag aaa gtg gcg gaa gtg ggc        1440
Gln Ile Glu Glu Leu Val Arg Leu Glu Glu Lys Val Ala Glu Val Gly
465                 470                 475                 480 atc act ggc ctg aac gct gac ttc ctg cgc cag ctg aaa cgc aaa ggc        1488
Ile Thr Gly Leu Asn Ala Asp Phe Leu Arg Gln Leu Lys Arg Lys Gly
                485                 490                 495 ttt gcc gat gcg cgc ttg gca aaa ctg gcg ggc gta cgc gaa gcg gaa        1536
Phe Ala Asp Ala Arg Leu Ala Lys Leu Ala Gly Val Arg Glu Ala Glu
            500                 505                 510 atc cgt aag ctg cgt gac cag tat gac ctg cac ccg gtt tat aag cgc        1584
Ile Arg Lys Leu Arg Asp Gln Tyr Asp Leu His Pro Val Tyr Lys Arg
        515                 520                 525 gtg gat acc tgt gcg gca gag ttc gcc acc gac acc gct tac atg tac        1632
Val Asp Thr Cys Ala Ala Glu Phe Ala Thr Asp Thr Ala Tyr Met Tyr
    530                 535                 540 tcc act tat gaa gaa gag tgc gaa gcg aat ccg tct acc gac cgt gaa        1680
Ser Thr Tyr Glu Glu Glu Cys Glu Ala Asn Pro Ser Thr Asp Arg Glu
545                 550                 555                 560 aaa atc atg gtg ctt ggc ggc ggc ccg aac cgt atc ggt cag ggt atc        1728
Lys Ile Met Val Leu Gly Gly Gly Pro Asn Arg Ile Gly Gln Gly Ile
                565                 570                 575 gaa ttc gac tac tgt tgc gta cac gcc tcg ctg gcg ctg cgc gaa gac        1776
Glu Phe Asp Tyr Cys Cys Val His Ala Ser Leu Ala Leu Arg Glu Asp
            580                 585                 590 ggt tac gaa acc att atg gtt aac tgt aac ccg gaa acc gtc tcc acc        1824
Gly Tyr Glu Thr Ile Met Val Asn Cys Asn Pro Glu Thr Val Ser Thr
        595                 600                 605 gac tac gac act tcc gac cgc ctc tac ttc gag ccg gta act ctg gaa        1872
Asp Tyr Asp Thr Ser Asp Arg Leu Tyr Phe Glu Pro Val Thr Leu Glu
    610                 615                 620 gat gtg ctg gaa atc gtg cgt atc gag aag ccg aaa ggc gtt atc gtc        1920
Asp Val Leu Glu Ile Val Arg Ile Glu Lys Pro Lys Gly Val Ile Val
625                 630                 635                 640 cag tac ggc ggt cag acc ccg ctg aaa ctg gcg cgc gcg ctg gaa gct        1968
Gln Tyr Gly Gly Gln Thr Pro Leu Lys Leu Ala Arg Ala Leu Glu Ala
                645                 650                 655 gct ggc gta ccg gtt atc ggc acc agc ccg gat gct atc gac cgt gca        2016
Ala Gly Val Pro Val Ile Gly Thr Ser Pro Asp Ala Ile Asp Arg Ala
            660                 665                 670
```

```
                                                              -continued gaa gac cgt gaa cgc ttc cag cat gcg gtt gag cgt ctg aaa ctg aaa      2064
Glu Asp Arg Glu Arg Phe Gln His Ala Val Glu Arg Leu Lys Leu Lys
            675                 680                 685 caa ccg gcg aac gcc acc gtt acc gct att gaa atg gcg gta gag aag      2112
Gln Pro Ala Asn Ala Thr Val Thr Ala Ile Glu Met Ala Val Glu Lys
        690                 695                 700 gcg aaa gag att ggc tac ccg ctg gtg gta cgt ccg tct tac gtt ctc      2160
Ala Lys Glu Ile Gly Tyr Pro Leu Val Val Arg Pro Ser Tyr Val Leu
705                 710                 715                 720 ggc ggt cgg gcg atg gaa atc gtc tat gac gaa gct gac ctg cgt cgc      2208
Gly Gly Arg Ala Met Glu Ile Val Tyr Asp Glu Ala Asp Leu Arg Arg
                725                 730                 735 tac ttc cag acg gcg gtc agc gtg tct aac gat gcg cca gtg ttg ctg      2256
Tyr Phe Gln Thr Ala Val Ser Val Ser Asn Asp Ala Pro Val Leu Leu
            740                 745                 750 gac cac ttc ctc gat gac gcg gta gaa gtt gac gtg gat gcc atc tgc      2304
Asp His Phe Leu Asp Asp Ala Val Glu Val Asp Val Asp Ala Ile Cys
        755                 760                 765 gac ggc gaa atg gtg ctg att ggc ggc atc atg gag cat att gag cag      2352
Asp Gly Glu Met Val Leu Ile Gly Gly Ile Met Glu His Ile Glu Gln
770                 775                 780 gcg ggc gtg cac tcc ggt gac tcc gca tgt tct ctg cca gcc tac acc      2400
Ala Gly Val His Ser Gly Asp Ser Ala Cys Ser Leu Pro Ala Tyr Thr
                785                 790                 795                 800 tta agt cag gaa att cag gat gtg atg cgc cag cag gtg cag aaa ctg      2448
Leu Ser Gln Glu Ile Gln Asp Val Met Arg Gln Gln Val Gln Lys Leu
            805                 810                 815 gcc ttc gaa ttg cag gtg cgc ggc ctg atg aac gtg cag ttt gcg gtg      2496
Ala Phe Glu Leu Gln Val Arg Gly Leu Met Asn Val Gln Phe Ala Val
        820                 825                 830 aaa aac aac gaa gtc tac ctg att gaa gtt aac ccg cgt gcg gcg cgt      2544
Lys Asn Asn Glu Val Tyr Leu Ile Glu Val Asn Pro Arg Ala Ala Arg
835                 840                 845 acc gtt ccg ttc gtc tcc aaa gcc acc ggc gta ccg ctg gca aaa gtg      2592
Thr Val Pro Phe Val Ser Lys Ala Thr Gly Val Pro Leu Ala Lys Val
        850                 855                 860 gcg gcg cgc gtg atg gct ggc aaa tcg ctg gct gag cag ggc gta acc      2640
Ala Ala Arg Val Met Ala Gly Lys Ser Leu Ala Glu Gln Gly Val Thr
865                 870                 875                 880 aaa gaa gtt atc ccg ccg tac tac tcg gtg aaa gaa gtg gtg ctg ccg      2688
Lys Glu Val Ile Pro Pro Tyr Tyr Ser Val Lys Glu Val Val Leu Pro
                885                 890                 895 ttc aat aaa ttc ccg ggc gtt gac ccg ctg tta ggg cca gaa atg cgc      2736
Phe Asn Lys Phe Pro Gly Val Asp Pro Leu Leu Gly Pro Glu Met Arg
            900                 905                 910 tct acc ggg gaa gtc atg ggc gtg ggc cgc acc ttc gct gaa gcg ttt      2784
Ser Thr Gly Glu Val Met Gly Val Gly Arg Thr Phe Ala Glu Ala Phe
        915                 920                 925 gcc aaa gcg cag ctg ggc agc aac tcc acc atg aag aaa cac ggt cgt      2832
Ala Lys Ala Gln Leu Gly Ser Asn Ser Thr Met Lys Lys His Gly Arg
930                 935                 940 gcg ctg ctt tcc gtg cgc gaa ggc gat aaa gaa cgc gtg gtg gac ctg      2880
Ala Leu Leu Ser Val Arg Glu Gly Asp Lys Glu Arg Val Val Asp Leu
                945                 950                 955                 960 gcg gca aaa ctg ctg aaa cag ggc ttc gag ctg gat gcg acc cac ggc      2928
Ala Ala Lys Leu Leu Lys Gln Gly Phe Glu Leu Asp Ala Thr His Gly
            965                 970                 975 acg gcg att gtg ctg ggc gaa gca ggt atc aac ccg cgt ctg gta aac      2976
Thr Ala Ile Val Leu Gly Glu Ala Gly Ile Asn Pro Arg Leu Val Asn
        980                 985                 990
```

```
aag gtg cat gaa ggc cgt ccg cac att cag gac cgt atc aag aat ggc    3024
Lys Val His Glu Gly Arg Pro His Ile Gln Asp Arg Ile Lys Asn Gly
        995                 1000                1005 gaa tat acc tac atc atc aac acc acc tca ggc cgt cgt gcg att        3069
Glu Tyr Thr Tyr Ile Ile Asn Thr Thr Ser Gly Arg Arg Ala Ile
    1010                1015                1020 gaa gac tcc cgc gtg att cgt cgc agt gcg ctg caa tat aaa gtg        3114
Glu Asp Ser Arg Val Ile Arg Arg Ser Ala Leu Gln Tyr Lys Val
1025                1030                1035 cat tac gac acc acc ctg aac ggc ggc ttt gcc acc gcg atg gcg        3159
His Tyr Asp Thr Thr Leu Asn Gly Gly Phe Ala Thr Ala Met Ala
    1040                1045                1050 ctg aat gcc gat gcg act gaa aaa gta att tcg gtg cag gaa atg        3204
Leu Asn Ala Asp Ala Thr Glu Lys Val Ile Ser Val Gln Glu Met
    1055                1060                1065 cac gca cag atc aaa taa                                            3222
His Ala Gln Ile Lys
    1070

<210> SEQ ID NO 20
<211> LENGTH: 1073
<212> TYPE: PRT
<213> ORGANISM: Escherichia coli

<400> SEQUENCE: 20

Met Pro Lys Arg Thr Asp Ile Lys Ser Ile Leu Ile Leu Gly Ala Gly
1               5                   10                  15

Pro Ile Val Ile Gly Gln Ala Cys Glu Phe Asp Tyr Ser Gly Ala Gln
            20                  25                  30

Ala Cys Lys Ala Leu Arg Glu Glu Gly Tyr Arg Val Ile Leu Val Asn
        35                  40                  45

Ser Asn Pro Ala Thr Ile Met Thr Asp Pro Glu Met Ala Asp Ala Thr
    50                  55                  60

Tyr Ile Glu Pro Ile His Trp Glu Val Val Arg Lys Ile Ile Glu Lys
65                  70                  75                  80

Glu Arg Pro Asp Ala Val Leu Pro Thr Met Gly Gly Gln Thr Ala Leu
                85                  90                  95

Asn Cys Ala Leu Glu Leu Glu Arg Gln Gly Val Leu Glu Glu Phe Gly
            100                 105                 110

Val Thr Met Ile Gly Ala Thr Ala Asp Ala Ile Asp Lys Ala Glu Asp
        115                 120                 125

Arg Arg Arg Phe Asp Val Ala Met Lys Lys Ile Gly Leu Glu Thr Ala
    130                 135                 140

Arg Ser Gly Ile Ala His Thr Met Glu Glu Ala Leu Ala Val Ala Ala
145                 150                 155                 160

Asp Val Gly Phe Pro Cys Ile Ile Arg Pro Ser Phe Thr Met Gly Gly
                165                 170                 175

Ser Gly Gly Gly Ile Ala Tyr Asn Arg Glu Glu Phe Glu Glu Ile Cys
            180                 185                 190

Ala Arg Gly Leu Asp Leu Ser Pro Thr Lys Glu Leu Leu Ile Asp Glu
        195                 200                 205

Ser Leu Ile Gly Trp Lys Glu Tyr Glu Met Glu Val Val Arg Asp Lys
    210                 215                 220

Asn Asp Asn Cys Ile Ile Val Cys Ser Ile Glu Asn Phe Asp Ala Met
225                 230                 235                 240

Gly Ile His Thr Gly Asp Ser Ile Thr Val Ala Pro Ala Gln Thr Leu
                245                 250                 255
```

-continued

```
Thr Asp Lys Glu Tyr Gln Ile Met Arg Asn Ala Ser Met Ala Val Leu
            260                 265                 270

Arg Glu Ile Gly Val Glu Thr Gly Gly Ser Asn Val Gln Phe Ala Val
        275                 280                 285

Asn Pro Lys Asn Gly Arg Leu Ile Val Ile Glu Met Asn Pro Arg Val
    290                 295                 300

Ser Arg Ser Ser Ala Leu Ala Ser Lys Ala Thr Gly Phe Pro Ile Ala
305                 310                 315                 320

Lys Val Ala Ala Lys Leu Ala Val Gly Tyr Thr Leu Asp Glu Leu Met
                325                 330                 335

Asn Asp Ile Thr Gly Gly Arg Thr Pro Ala Ser Phe Glu Pro Ser Ile
            340                 345                 350

Asp Tyr Val Val Thr Lys Ile Pro Arg Phe Asn Phe Glu Lys Phe Ala
        355                 360                 365

Gly Ala Asn Asp Arg Leu Thr Thr Gln Met Lys Ser Val Gly Glu Val
    370                 375                 380

Met Ala Ile Gly Arg Thr Gln Gln Glu Ser Leu Gln Lys Ala Leu Arg
385                 390                 395                 400

Gly Leu Glu Val Gly Ala Thr Gly Phe Asp Pro Lys Val Ser Leu Asp
                405                 410                 415

Asp Pro Glu Ala Leu Thr Lys Ile Arg Arg Glu Leu Lys Asp Ala Gly
            420                 425                 430

Ala Asp Arg Ile Trp Tyr Ile Ala Asp Ala Phe Arg Ala Gly Leu Ser
        435                 440                 445

Val Asp Gly Val Phe Asn Leu Thr Asn Ile Asp Arg Trp Phe Leu Val
    450                 455                 460

Gln Ile Glu Glu Leu Val Arg Leu Glu Glu Lys Val Ala Glu Val Gly
465                 470                 475                 480

Ile Thr Gly Leu Asn Ala Asp Phe Leu Arg Gln Leu Lys Arg Lys Gly
                485                 490                 495

Phe Ala Asp Ala Arg Leu Ala Lys Leu Ala Gly Val Arg Glu Ala Glu
            500                 505                 510

Ile Arg Lys Leu Arg Asp Gln Tyr Asp Leu His Pro Val Tyr Lys Arg
        515                 520                 525

Val Asp Thr Cys Ala Ala Glu Phe Ala Thr Asp Thr Ala Tyr Met Tyr
    530                 535                 540

Ser Thr Tyr Glu Glu Glu Cys Glu Ala Asn Pro Ser Thr Asp Arg Glu
545                 550                 555                 560

Lys Ile Met Val Leu Gly Gly Pro Asn Arg Ile Gly Gln Gly Ile
                565                 570                 575

Glu Phe Asp Tyr Cys Cys Val His Ala Ser Leu Ala Leu Arg Glu Asp
            580                 585                 590

Gly Tyr Glu Thr Ile Met Val Asn Cys Asn Pro Glu Thr Val Ser Thr
        595                 600                 605

Asp Tyr Asp Thr Ser Asp Arg Leu Tyr Phe Glu Pro Val Thr Leu Glu
    610                 615                 620

Asp Val Leu Glu Ile Val Arg Ile Glu Lys Pro Lys Gly Val Ile Val
625                 630                 635                 640

Gln Tyr Gly Gly Gln Thr Pro Leu Lys Leu Ala Arg Ala Leu Glu Ala
                645                 650                 655

Ala Gly Val Pro Val Ile Gly Thr Ser Pro Asp Ala Ile Asp Arg Ala
            660                 665                 670
```

```
Glu Asp Arg Glu Arg Phe Gln His Ala Val Glu Arg Leu Lys Leu Lys
        675                 680                 685

Gln Pro Ala Asn Ala Thr Val Thr Ala Ile Glu Met Ala Val Glu Lys
    690                 695                 700

Ala Lys Glu Ile Gly Tyr Pro Leu Val Val Arg Pro Ser Tyr Val Leu
705                 710                 715                 720

Gly Gly Arg Ala Met Glu Ile Val Tyr Asp Glu Ala Asp Leu Arg Arg
                725                 730                 735

Tyr Phe Gln Thr Ala Val Ser Val Ser Asn Asp Ala Pro Val Leu Leu
            740                 745                 750

Asp His Phe Leu Asp Asp Ala Val Glu Val Asp Val Asp Ala Ile Cys
        755                 760                 765

Asp Gly Glu Met Val Leu Ile Gly Gly Ile Met Glu His Ile Glu Gln
770                 775                 780

Ala Gly Val His Ser Gly Asp Ser Ala Cys Ser Leu Pro Ala Tyr Thr
785                 790                 795                 800

Leu Ser Gln Glu Ile Gln Asp Val Met Arg Gln Val Gln Lys Leu
                805                 810                 815

Ala Phe Glu Leu Gln Val Arg Gly Leu Met Asn Val Gln Phe Ala Val
                820                 825                 830

Lys Asn Asn Glu Val Tyr Leu Ile Glu Val Asn Pro Arg Ala Ala Arg
835                 840                 845

Thr Val Pro Phe Val Ser Lys Ala Thr Gly Val Pro Leu Ala Lys Val
        850                 855                 860

Ala Ala Arg Val Met Ala Gly Lys Ser Leu Ala Glu Gln Gly Val Thr
865                 870                 875                 880

Lys Glu Val Ile Pro Pro Tyr Tyr Ser Val Lys Glu Val Val Leu Pro
                885                 890                 895

Phe Asn Lys Phe Pro Gly Val Asp Pro Leu Leu Gly Pro Glu Met Arg
                900                 905                 910

Ser Thr Gly Glu Val Met Gly Val Gly Arg Thr Phe Ala Glu Ala Phe
        915                 920                 925

Ala Lys Ala Gln Leu Gly Ser Asn Ser Thr Met Lys Lys His Gly Arg
930                 935                 940

Ala Leu Leu Ser Val Arg Glu Gly Asp Lys Glu Arg Val Val Asp Leu
945                 950                 955                 960

Ala Ala Lys Leu Leu Lys Gln Gly Phe Glu Leu Asp Ala Thr His Gly
                965                 970                 975

Thr Ala Ile Val Leu Gly Glu Ala Gly Ile Asn Pro Arg Leu Val Asn
            980                 985                 990

Lys Val His Glu Gly Arg Pro His Ile Gln Asp Arg Ile Lys Asn Gly
        995                 1000                1005

Glu Tyr Thr Tyr Ile Ile Asn Thr Thr Ser Gly Arg Arg Ala Ile
    1010                1015                1020

Glu Asp Ser Arg Val Ile Arg Arg Ser Ala Leu Gln Tyr Lys Val
    1025                1030                1035

His Tyr Asp Thr Thr Leu Asn Gly Gly Phe Ala Thr Ala Met Ala
    1040                1045                1050

Leu Asn Ala Asp Ala Thr Glu Lys Val Ile Ser Val Gln Glu Met
    1055                1060                1065

His Ala Gln Ile Lys
    1070
```

-continued

<210> SEQ ID NO 21
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 21
accagatctg cgggcagtga gcgcaacgc                              29

<210> SEQ ID NO 22
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 22
gtttctagat cctgtgtgaa attgttatcc gc                          32

<210> SEQ ID NO 23
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 23
cctctagaaa taaagtgagt gaatattc                               28

<210> SEQ ID NO 24
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 24
cttagcggtt ttacggtact gc                                     22

<210> SEQ ID NO 25
<211> LENGTH: 48
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (13)..(13)
<223> OTHER INFORMATION: n = a or g or t or c
<220> FEATURE:
<221> NAME/KEY: misc_feature
<222> LOCATION: (14)..(14)
<223> OTHER INFORMATION: n = a or g or t or c
<220> FEATURE:
<221> NAME/KEY: misc_feature
<222> LOCATION: (16)..(16)
<223> OTHER INFORMATION: n = a or g or t or c
<220> FEATURE:
<221> NAME/KEY: misc_feature
<222> LOCATION: (19)..(19)
<223> OTHER INFORMATION: n = a or g or t or c
<220> FEATURE:
<221> NAME/KEY: misc_feature
<222> LOCATION: (20)..(20)
<223> OTHER INFORMATION: n = a or g or t or c
<220> FEATURE:
<221> NAME/KEY: misc_feature
<222> LOCATION: (22)..(22)
<223> OTHER INFORMATION: n = a or g or t or c

```
<220> FEATURE:
<221> NAME/KEY: misc_feature
<222> LOCATION: (23)..(23)
<223> OTHER INFORMATION: n = a or g or t or c
<220> FEATURE:
<221> NAME/KEY: misc_feature
<222> LOCATION: (24)..(24)
<223> OTHER INFORMATION: n = a or g or t or c
<220> FEATURE:
<221> NAME/KEY: misc_feature
<222> LOCATION: (26)..(26)
<223> OTHER INFORMATION: n = a or g or t or c
<220> FEATURE:
<221> NAME/KEY: misc_feature
<222> LOCATION: (27)..(27)
<223> OTHER INFORMATION: n = a or g or t or c

<400> SEQUENCE: 25
ggtcgtgcgc tgnnynycnn ynnnrnnggc gataaagaac gcgtggtg        48

<210> SEQ ID NO 26
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 26
ccacttcctc gatgacgcgg                                       20

<210> SEQ ID NO 27
<211> LENGTH: 34
<212> TYPE: DNA
<213> ORGANISM: ARTIFICIAL SEQUENCE
<220> FEATURE:
<223> OTHER INFORMATION: SYNTHETIC DNA

<400> SEQUENCE: 27
cgtgcgctgc ttttcgtgcg cgaaggcgat aaag                       34

<210> SEQ ID NO 28
<211> LENGTH: 5
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 28

Leu Ser Val Arg Glu
1               5

<210> SEQ ID NO 29
<211> LENGTH: 5
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 29

Leu Phe Val Arg Glu
1               5

<210> SEQ ID NO 30
<211> LENGTH: 15
<212> TYPE: DNA
<213> ORGANISM: ARTIFICIAL SEQUENCE
<220> FEATURE:
<223> OTHER INFORMATION: SYNTHETIC DNA
```

-continued

```
<210> SEQ ID NO 31
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 31
cttttcgtgc gcgaa                                                        15

<210> SEQ ID NO 32
<211> LENGTH: 1149
<212> TYPE: DNA
<213> ORGANISM: Escherichia coli
<220> FEATURE:
<221> NAME/KEY: CDS
<222> LOCATION: (1)..(1149)
<223> OTHER INFORMATION:

<400> SEQUENCE: 32
```

```
<400> SEQUENCE: 30
ctttccgtgc gcgaa                                                        15
```

```
ttg att aag tca gcg cta ttg gtt ctg gaa gac gga acc cag ttt cac          48
Leu Ile Lys Ser Ala Leu Leu Val Leu Glu Asp Gly Thr Gln Phe His
1               5                   10                  15 ggt cgg gcc ata ggg gca aca ggt tcg gcg gtt ggg gaa gtc gtt ttc          96
Gly Arg Ala Ile Gly Ala Thr Gly Ser Ala Val Gly Glu Val Val Phe
            20                  25                  30 aat act tca atg acc ggt tat caa gaa atc ctc act gat cct tcc tat         144
Asn Thr Ser Met Thr Gly Tyr Gln Glu Ile Leu Thr Asp Pro Ser Tyr
        35                  40                  45 tct cgt caa atc gtt act ctt act tat ccc cat att ggc aat gtc ggc         192
Ser Arg Gln Ile Val Thr Leu Thr Tyr Pro His Ile Gly Asn Val Gly
    50                  55                  60 acc aat gac gcc gat gaa gaa tct tct cag gta cat gca caa ggt ctg         240
Thr Asn Asp Ala Asp Glu Glu Ser Ser Gln Val His Ala Gln Gly Leu
65                  70                  75                  80 gtg att cgc gac ctg ccg ctg att gcc agc aac ttc cgt aat acc gaa         288
Val Ile Arg Asp Leu Pro Leu Ile Ala Ser Asn Phe Arg Asn Thr Glu
                85                  90                  95 gac ctc tct tct tac ctg aaa cgc cat aac atc gtg gcg att gcc gat         336
Asp Leu Ser Ser Tyr Leu Lys Arg His Asn Ile Val Ala Ile Ala Asp
            100                 105                 110 atc gat acc cgt aag ctg acg cgt tta ctg cgc gag aaa ggc gca cag         384
Ile Asp Thr Arg Lys Leu Thr Arg Leu Leu Arg Glu Lys Gly Ala Gln
        115                 120                 125 aat ggc tgc att atc gcg ggc gat aac ccg gat gcg gcg ctg gcg tta         432
Asn Gly Cys Ile Ile Ala Gly Asp Asn Pro Asp Ala Ala Leu Ala Leu
    130                 135                 140 gaa aaa gcc cgc gcg ttc cca ggt ctg aat ggc atg gat ctg gca aaa         480
Glu Lys Ala Arg Ala Phe Pro Gly Leu Asn Gly Met Asp Leu Ala Lys
145                 150                 155                 160 gaa gtg acc acc gca gaa gcc tat agc tgg aca caa ggg agc tgg acg         528
Glu Val Thr Thr Ala Glu Ala Tyr Ser Trp Thr Gln Gly Ser Trp Thr
                165                 170                 175 ttg acc ggt ggc ctg cca gaa gcg aaa aaa gaa gac gag ctg ccg ttc         576
Leu Thr Gly Gly Leu Pro Glu Ala Lys Lys Glu Asp Glu Leu Pro Phe
            180                 185                 190 cac gtc gtg gct tat gat ttt ggt gcc aag cgc aac atc ctg cgg atg         624
His Val Val Ala Tyr Asp Phe Gly Ala Lys Arg Asn Ile Leu Arg Met
        195                 200                 205
```

-continued

```
ctg gtg gat aga ggc tgt cgc ctg acc atc gtt ccg gcg caa act tct         672
Leu Val Asp Arg Gly Cys Arg Leu Thr Ile Val Pro Ala Gln Thr Ser
    210                 215                 220 gcg gaa gat gtg ctg aaa atg aat cca gac ggc atc ttc ctc tcc aac         720
Ala Glu Asp Val Leu Lys Met Asn Pro Asp Gly Ile Phe Leu Ser Asn
225                 230                 235                 240 ggt cct ggc gac ccg gcc ccg tgc gat tac gcc att acc gcc atc cag         768
Gly Pro Gly Asp Pro Ala Pro Cys Asp Tyr Ala Ile Thr Ala Ile Gln
                245                 250                 255 aaa ttc ctc gaa acc gat att ccg gta ttc ggc atc tgt ctc ggt cat         816
Lys Phe Leu Glu Thr Asp Ile Pro Val Phe Gly Ile Cys Leu Gly His
            260                 265                 270 cag ctg ctg gcg ctg gcg agc ggt gcg aag act gtc aaa atg aaa ttt         864
Gln Leu Leu Ala Leu Ala Ser Gly Ala Lys Thr Val Lys Met Lys Phe
        275                 280                 285 ggt cac cac ggc ggc aac cat ccg gtt aaa gat gtg gag aaa aac gtg         912
Gly His His Gly Gly Asn His Pro Val Lys Asp Val Glu Lys Asn Val
    290                 295                 300 gta atg atc acc gcc cag aac cac ggt ttt gcg gtg gac gaa gca aca         960
Val Met Ile Thr Ala Gln Asn His Gly Phe Ala Val Asp Glu Ala Thr
305                 310                 315                 320 tta cct gca aac ctg cgt gtc acg cat aaa tcc ctg ttc gac ggt acg        1008
Leu Pro Ala Asn Leu Arg Val Thr His Lys Ser Leu Phe Asp Gly Thr
                325                 330                 335 tta cag ggc att cat cgc acc gat aaa ccg gca ttc agc ttc cag ggg        1056
Leu Gln Gly Ile His Arg Thr Asp Lys Pro Ala Phe Ser Phe Gln Gly
            340                 345                 350 cac cct gaa gcc agc cct ggt cca cac gac gcc gcg ccg ttg ttc gac        1104
His Pro Glu Ala Ser Pro Gly Pro His Asp Ala Ala Pro Leu Phe Asp
        355                 360                 365 cac ttt atc gag tta att gag cag tac cgt aaa acc gct aag taa            1149
His Phe Ile Glu Leu Ile Glu Gln Tyr Arg Lys Thr Ala Lys
    370                 375                 380

<210> SEQ ID NO 33
<211> LENGTH: 382
<212> TYPE: PRT
<213> ORGANISM: Escherichia coli

<400> SEQUENCE: 33

Leu Ile Lys Ser Ala Leu Leu Val Leu Glu Asp Gly Thr Gln Phe His
1               5                   10                  15

Gly Arg Ala Ile Gly Ala Thr Gly Ser Ala Val Gly Glu Val Val Phe
                20                  25                  30

Asn Thr Ser Met Thr Gly Tyr Gln Glu Ile Leu Thr Asp Pro Ser Tyr
            35                  40                  45

Ser Arg Gln Ile Val Thr Leu Thr Tyr Pro His Ile Gly Asn Val Gly
        50                  55                  60

Thr Asn Asp Ala Asp Glu Glu Ser Ser Gln Val His Ala Gln Gly Leu
65                  70                  75                  80

Val Ile Arg Asp Leu Pro Leu Ile Ala Ser Asn Phe Arg Asn Thr Glu
                85                  90                  95

Asp Leu Ser Ser Tyr Leu Lys Arg His Asn Ile Val Ala Ile Ala Asp
            100                 105                 110

Ile Asp Thr Arg Lys Leu Thr Arg Leu Leu Arg Glu Lys Gly Ala Gln
        115                 120                 125

Asn Gly Cys Ile Ile Ala Gly Asp Asn Pro Asp Ala Ala Leu Ala Leu
    130                 135                 140
```

-continued

| | | | | | | | | | | | | | | | |
|---|---|---|---|---|---|---|---|---|---|---|---|---|---|---|---|
| Glu | Lys | Ala | Arg | Ala | Phe | Pro | Gly | Leu | Asn | Gly | Met | Asp | Leu | Ala | Lys |
| 145 | | | | | 150 | | | | 155 | | | | | | 160 |
| Glu | Val | Thr | Thr | Ala | Glu | Ala | Tyr | Ser | Trp | Thr | Gln | Gly | Ser | Trp | Thr |
| | | | | 165 | | | | | 170 | | | | 175 | | |
| Leu | Thr | Gly | Gly | Leu | Pro | Glu | Ala | Lys | Lys | Glu | Asp | Glu | Leu | Pro | Phe |
| | | | 180 | | | | | 185 | | | | | 190 | | |
| His | Val | Val | Ala | Tyr | Asp | Phe | Gly | Ala | Lys | Arg | Asn | Ile | Leu | Arg | Met |
| | | 195 | | | | | 200 | | | | | 205 | | | |
| Leu | Val | Asp | Arg | Gly | Cys | Arg | Leu | Thr | Ile | Val | Pro | Ala | Gln | Thr | Ser |
| | 210 | | | | 215 | | | | | 220 | | | | | |
| Ala | Glu | Asp | Val | Leu | Lys | Met | Asn | Pro | Asp | Gly | Ile | Phe | Leu | Ser | Asn |
| 225 | | | | 230 | | | | | 235 | | | | | | 240 |
| Gly | Pro | Gly | Asp | Pro | Ala | Pro | Cys | Asp | Tyr | Ala | Ile | Thr | Ala | Ile | Gln |
| | | | 245 | | | | | 250 | | | | | 255 | | |
| Lys | Phe | Leu | Glu | Thr | Asp | Ile | Pro | Val | Phe | Gly | Ile | Cys | Leu | Gly | His |
| | | | 260 | | | | | 265 | | | | | 270 | | |
| Gln | Leu | Leu | Ala | Leu | Ala | Ser | Gly | Ala | Lys | Thr | Val | Lys | Met | Lys | Phe |
| | | 275 | | | | | 280 | | | | | 285 | | | |
| Gly | His | His | Gly | Gly | Asn | His | Pro | Val | Lys | Asp | Val | Glu | Lys | Asn | Val |
| | 290 | | | | | 295 | | | | | 300 | | | | |
| Val | Met | Ile | Thr | Ala | Gln | Asn | His | Gly | Phe | Ala | Val | Asp | Glu | Ala | Thr |
| 305 | | | | | 310 | | | | 315 | | | | | | 320 |
| Leu | Pro | Ala | Asn | Leu | Arg | Val | Thr | His | Lys | Ser | Leu | Phe | Asp | Gly | Thr |
| | | | | 325 | | | | | 330 | | | | | 335 | |
| Leu | Gln | Gly | Ile | His | Arg | Thr | Asp | Lys | Pro | Ala | Phe | Ser | Phe | Gln | Gly |
| | | | 340 | | | | | 345 | | | | | 350 | | |
| His | Pro | Glu | Ala | Ser | Pro | Gly | Pro | His | Asp | Ala | Ala | Pro | Leu | Phe | Asp |
| | | 355 | | | | | 360 | | | | | 365 | | | |
| His | Phe | Ile | Glu | Leu | Ile | Glu | Gln | Tyr | Arg | Lys | Thr | Ala | Lys | | |
| | 370 | | | | | 375 | | | | | 380 | | | | |